(12) United States Patent
Steiner et al.

(10) Patent No.: US 8,062,293 B2
(45) Date of Patent: Nov. 22, 2011

(54) STRUT JOINT FOR AN EXTERNAL FIXATOR

(75) Inventors: Christian Steiner, Eisenach (DE); Beat Knuchel, Ursenbach (CH); Meinrad Fiechter, Münsingen (CH); Vinzenz Burgherr, Wabern (CH)

(73) Assignee: Stryker Trauma SA (CH)

( * ) Notice: Subject to any disclaimer, the term of this patent is extended or adjusted under 35 U.S.C. 154(b) by 471 days.

(21) Appl. No.: 12/288,332

(22) Filed: Oct. 17, 2008

(65) Prior Publication Data
US 2009/0198235 A1  Aug. 6, 2009

(30) Foreign Application Priority Data

Feb. 1, 2008  (EP) .................................. 08150971

(51) Int. Cl.
*A61B 17/00* (2006.01)
(52) U.S. Cl. ......................................................... 606/54
(58) Field of Classification Search ............... 606/54–59; 403/76, 90, 109.5, 109.8, 367, 368, 374.1
See application file for complete search history.

(56) References Cited

U.S. PATENT DOCUMENTS

| | | | |
|---|---|---|---|
| 2,291,747 A | | 8/1942 | Neuwirth |
| 2,883,219 A | | 4/1959 | Cox |
| 3,691,788 A | * | 9/1972 | Mazziotti ........................ 464/139 |
| 3,977,397 A | | 8/1976 | Kalnberz et al. |
| 4,308,863 A | | 1/1982 | Fischer |
| 4,520,983 A | * | 6/1985 | Templeman .................. 248/481 |
| 4,615,338 A | | 10/1986 | Ilizarov et al. |
| 4,978,348 A | | 12/1990 | Ilizarov et al. |
| 5,087,258 A | | 2/1992 | Schewior |
| 5,466,237 A | | 11/1995 | Byrd, III et al. |
| 5,702,389 A | | 12/1997 | Taylor et al. |
| 5,728,095 A | * | 3/1998 | Taylor et al. ..................... 606/54 |
| 5,863,292 A | * | 1/1999 | Tosic ............................... 606/56 |

(Continued)

FOREIGN PATENT DOCUMENTS
EP 0377744 7/1990
(Continued)

OTHER PUBLICATIONS

Alizade et al., Mech. Mach. Theory, vol. 29, No. 1, pp. 115-124, 1994, Great Britain.

(Continued)

*Primary Examiner* — Eduardo C Robert
*Assistant Examiner* — Jacqueline Johanas
(74) *Attorney, Agent, or Firm* — Lerner, David, Littenberg, Krumholz & Mentlik, LLP

(57) ABSTRACT

A ball joint for use with an external fixator has a sleeve in engagement with a rod of a strut for the external fixator. A ring insert and a blocking element are provided, having a combined circumferential surface being able to be introduced into a hole of a ring of an external fixator. The ring insert and blocking element have complementary wedge surfaces allowing a relative radial displacement therebetween to enlarge the diameter of the combined circumferential surface for blocking the ball joint inside the hole. Additionally the sleeve comprises a spherical hollow ball portion with concentrical inner and outer spherical portions, wherein the outer spherical portion engages a complementary spherical socket of the blocking element and wherein the inner spherical portion is engaged by a ball nut. A connection element extends through the sleeve, blocking element and ring insert, wherein a radial displacement and axial displacement of the ring insert and blocking element are activated by the connection element.

11 Claims, 5 Drawing Sheets

U.S. PATENT DOCUMENTS

| | | | |
|---|---|---|---|
| 6,021,579 A | 2/2000 | Schimmels et al. | |
| 6,030,386 A | 2/2000 | Taylor et al. | |
| 6,090,111 A | 7/2000 | Nichols | |
| 6,176,860 B1 * | 1/2001 | Howard | 606/54 |
| 6,371,957 B1 | 4/2002 | Amrein et al. | |
| 6,565,565 B1 | 5/2003 | Yuan et al. | |
| 6,565,567 B1 | 5/2003 | Haider | |
| 6,701,174 B1 | 3/2004 | Krause et al. | |
| 6,733,502 B2 | 5/2004 | Altarac et al. | |
| 7,022,122 B2 | 4/2006 | Amrein et al. | |
| 7,197,806 B2 | 4/2007 | Boudreaux et al. | |
| 7,282,052 B2 | 10/2007 | Mullaney | |
| 7,306,601 B2 | 12/2007 | McGrath et al. | |
| 7,377,923 B2 | 5/2008 | Purcell et al. | |
| 7,422,593 B2 | 9/2008 | Cresina et al. | |
| 2001/0025181 A1 * | 9/2001 | Freedlan | 606/73 |
| 2002/0010465 A1 | 1/2002 | Koo et al. | |
| 2003/0063949 A1 | 4/2003 | Hohenocker | |
| 2005/0015087 A1 | 1/2005 | Walulik et al. | |
| 2005/0084325 A1 * | 4/2005 | O'Brien et al. | 403/322.1 |
| 2005/0248156 A1 | 11/2005 | Hsieh | |
| 2005/0251136 A1 | 11/2005 | Noon et al. | |
| 2006/0184169 A1 | 8/2006 | Stevens | |
| 2006/0243873 A1 | 11/2006 | Carnevali | |
| 2006/0247622 A1 * | 11/2006 | Maughan et al. | 606/61 |
| 2006/0247629 A1 | 11/2006 | Maughan et al. | |
| 2006/0261221 A1 * | 11/2006 | Carnevali | 248/159 |
| 2007/0162022 A1 | 7/2007 | Zhang et al. | |
| 2008/0021451 A1 | 1/2008 | Coull et al. | |
| 2009/0198235 A1 | 8/2009 | Steiner et al. | |
| 2010/0087819 A1 | 4/2010 | Mullaney | |

FOREIGN PATENT DOCUMENTS

| | | |
|---|---|---|
| EP | 1016381 | 12/2003 |
| FR | 2439002 | 5/1980 |
| FR | 2576774 | 8/1986 |
| FR | 2756025 A1 | 5/1998 |
| IT | 1259768 | 3/1996 |
| WO | WO-01/78613 | 10/2001 |

OTHER PUBLICATIONS

European Search Report, EP 08 15 0944.
European Search Report, EP 08 15 0971.
European Search Report, EP 09 15 0507.
International Search Report and Written Opinion, PCT/US2010/000712, dated Jun. 28, 2010.
Smith&Nephew, Taylor Spatial Frame, website printout, Aug. 12, 2009.

* cited by examiner

STRUT JOINT FOR AN EXTERNAL FIXATOR

BACKGROUND OF THE INVENTION

The invention relates to a ball joint for a rod, especially a telescopic rod for an external fixator, especially for use with an external ring fixator. It is further related to a strut comprising a rod and two ball or universal joints at the free ends of the rod.

A plurality of compression-distraction apparatus have been designed and improved by Ilizarov and his group using two external rings to be placed around the limb to be fixed. There are usually at least two such rings, one proximal and one distal ring, which are connected with a plurality of struts or rods. Preferably, these struts are linked to the rings in a way that the attachment points can be pivoted and the length of the strut can be varied to enable adjustment of the external fixation rings.

Ilizarov has also provided some improvements for said systems. EP 0 377 744 shows a telescopic rod for such an external fixator. U.S. Pat. No. 4,615,338 shows a further device to control the length of such telescopic rods. The rods are extending through the rings and are attached to said rings via nuts. The use of said devices is inconvenient since the two rings, between which the struts are to be arranged, need to be in nearly perfect orientation to fit the straight rods through the ring holes of said rings.

A different external ring fixator having telescopic rods is shown in U.S. Pat. No. 5,702,389. There the connection between the rods and the two related rings use a different structure. That patent discloses spheres incorporated into the ring system, being half-spheres attaching two rods to such a hole. Further, in order to achieve adjustability, one part of the connector is introduced into a hole of the fixator ring and consists of a flexible material which then attaches to the rod part of the strut. This allows for pivotal connection of said rod/strut to one hole of the ring of the fixator.

SUMMARY OF THE INVENTION

However, there is still a need for improved universal joints for that use, i.e. joints being able to allow moving attached struts in (almost) every direction, which is necessary, when the telescopic struts are shortened or lengthened or—being connected to such a manipulation—if the two rings are positioned in a different direction and orientation in space. It is one aspect of the invention to improve the ease of using such rods with a ring fixator, especially to fit the struts into the holes if they are at least in a certain area, not necessarily at the ideal place, and that these rings can stay angulated to each other.

It is therefore one aspect of the invention to provide a joint for a strut of an external fixator, especially a ball joint for a telescopic rod for a ring fixator, which can be readily and quickly changed in its orientation as well as securely fixed in a determined orientation.

It is a further object of the invention to provide a strut comprising such ball joints for allowing an easy connection of two rings of an external fixator.

The invention provides inter alia a ball joint for use with an external fixator comprising a sleeve being in engagement with a rod of a strut for said external fixator. A ring insert and a blocking element are provided, having a combined circumferential surface being able to be introduced into a hole of an external fixator element, especially into a hole of a ring of an external fixator. Ring insert and blocking element have complementary wedge surfaces allowing a relative radial displacement of ring insert and blocking element one against the other to enlarge the diameter of the combined circumferential surface for blocking the ball joint inside such a hole. Additionally sleeve comprises a spherical hollow ball portion with concentrical inner and outer spherical portions, wherein the outer spherical portion engages a complementary spherical socket of blocking element and wherein the inner spherical portion is engaged by a ball nut. The ball nut is in an axial displaceable relationship with a connection element extending in and through sleeve, blocking element and ring insert, wherein the radial displacement and axial displacement are activated by the connection element.

The ball joint according to the invention combines two functions. A first function is to lock and unlock the rotation of the ball joint. A second function of the joint relates to the fixation of the joint and with the joint the rod and thus one end of the connecting strut within a cylindrical hole of a ring fixator.

It is an advantage of the present invention to allow the tightening step of both functions to be executed with one movement. For a complete loosening of the device usually two operations are necessary due to the self locking property of the hole fixation.

BRIEF DESCRIPTION OF THE DRAWINGS

The invention is now described with reference to the enclosed drawings, showing preferred embodiments of the joint in connection with a telescopic rod.

DETAILED DESCRIPTION

Figure 1:
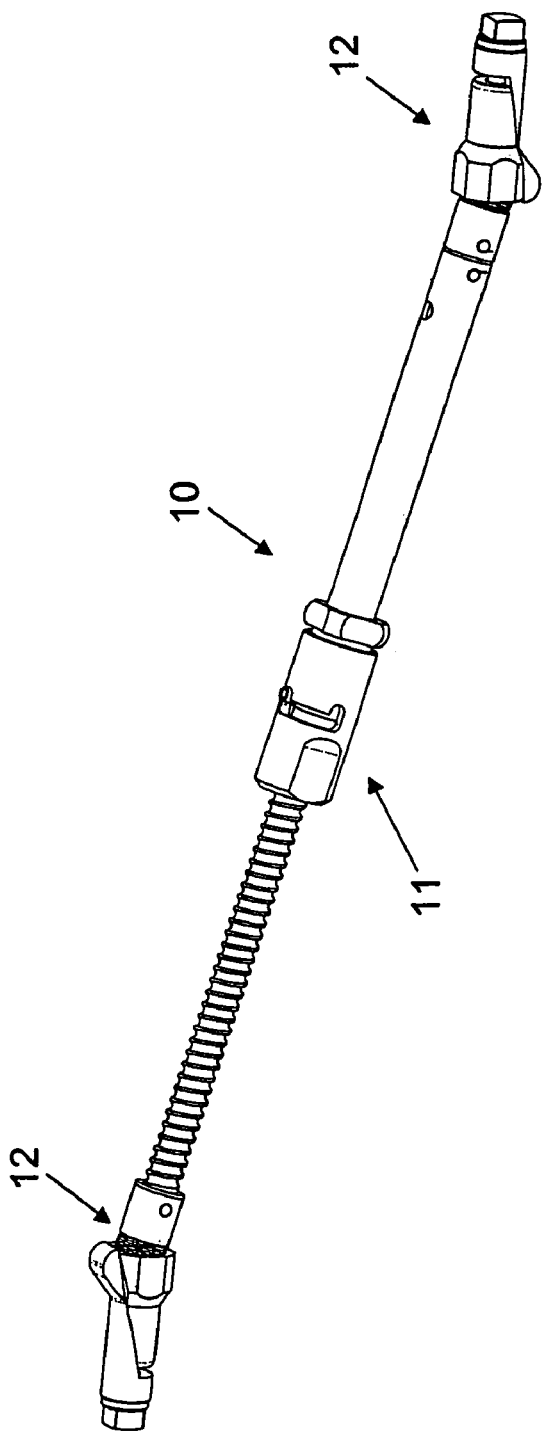
FIG. 1 is a perspective view of a strut comprising two ball joints, according to the invention.
Figure 4:
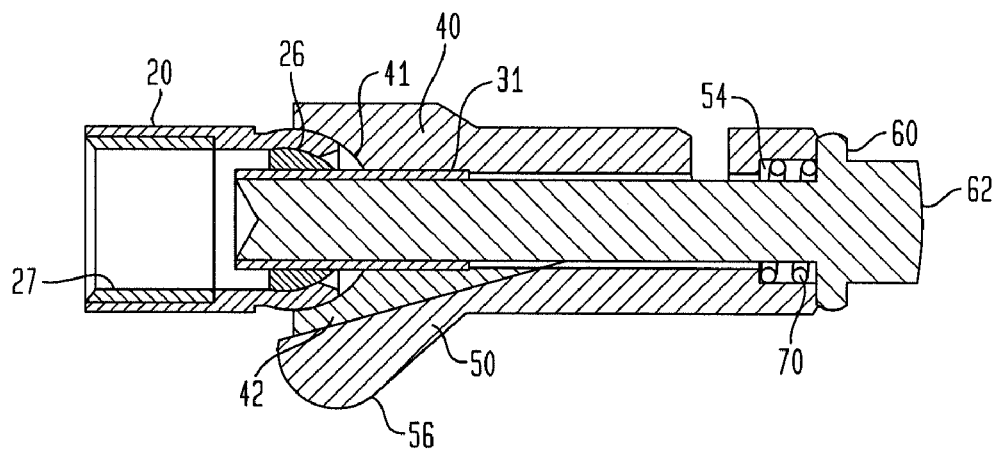
FIG. 4 is a cross section of the joint according to FIG. 2 in its longitudinal direction.

FIG. 1 shows a perspective view of a strut 10 comprising a rod 11 and two ball joints 12, according to an embodiment of the invention. The strut 10 comprises usually a plurality of single elements, as can be seen for the ball joint in FIG. 2. Preferably, the strut 10 comprises three units, rod 11 and two joints 12, which are usually connected either with an element of the rod 11 being also part of a corresponding joint 12 or wherein the joint is connected with a screw or bayonet connection with the rod 11. FIG. 4 shows an inner rod connection thread 27.

Figure 2:
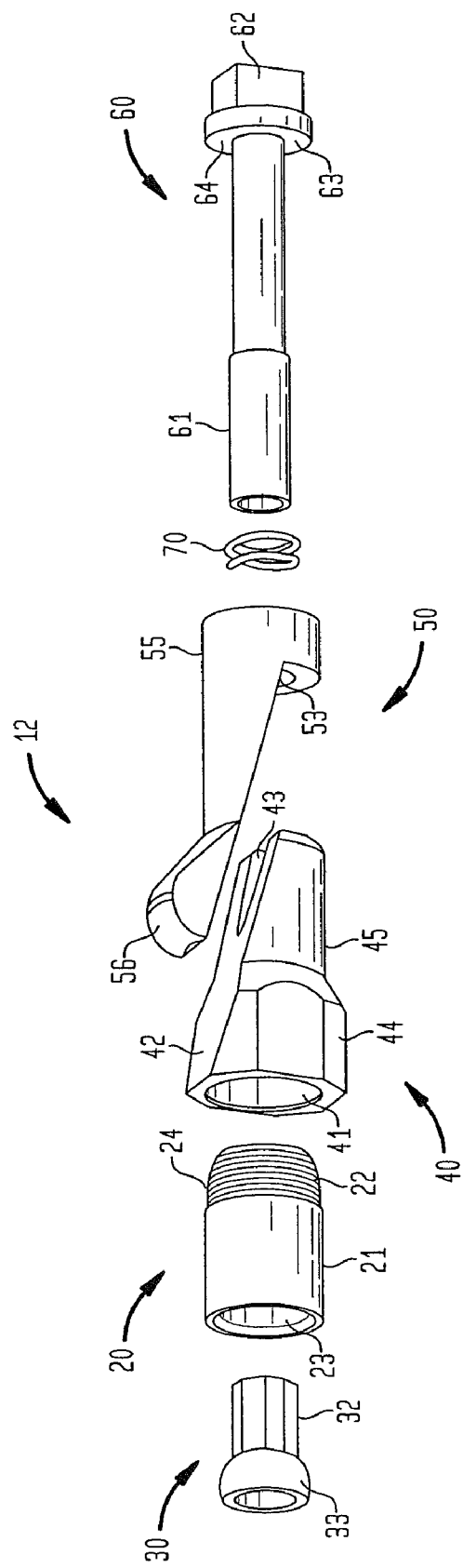
FIG. 2 is a perspective exploded view of a joint according to the invention as used in FIG. 1.

FIG. 2 shows a perspective view of a ball joint 12 according to an embodiment of the invention. As mentioned above the ball joint 12 comprises a sleeve 20 being connected to a rod 11 of the strut 10 in a predetermined way. This can be done in many ways known to the person skilled in the art. Sleeve 20 of FIG. 2 therefore comprises a cylindrical portion 21 which can be part of the rod 11 or is connected thereto at its free end, where ball nut 30 is shown in FIG. 2. Ball nut 30 comprises a polygonal rod or cylinder 32, i.e. a mathematical so called generalized cylinder having a polygon as basic top and bottom surface, followed by a spherical portion 33. The basic polygon of the generalized cylinder can be an octagon. Here the basic circle of the cross-section has received four flat surfaces, wherein neighbouring surfaces are in a 90 degree angle one to another, i.e. like a tetragon, with intervening spherical portions. The engagement of ball nut 30 inside sleeve blocking element 40 will be explained in connection with FIG. 3.

Sleeve 20 comprises at the opposite side a ball like element, which is called ball 22 in the subsequent description.

Ball 22, thus being indirectly fixedly connected to rod 11, is rotatable within a socket 41 of blocking element 40. Blocking element 40 comprises a first inclined surface 42 being complementary to a second inclined surface 52 being part of a ring insert 50. All three elements, sleeve 20, blocking element 40 as well as ring insert 50 have a central bore, indicated through reference numerals 23, 43 and 53, respectively. Opposite to ball nut 30 a fixation screw 60 is provided, extending through all of the above-mentioned bores 23, 43 and 53 and threaded with its outer thread 61 into the inner thread 31 of ball nut 30, not shown in FIG. 2 but visible in FIG. 4. Furthermore a spring 70 is shown in FIG. 2 being arranged between two abutment shoulders 64 and 54 of fixation screw 60 and ring insert 50, respectively. Abutment shoulder 64 is provided by flange 63 which is near the screw head, using a square-head end 62.

Figure 3:
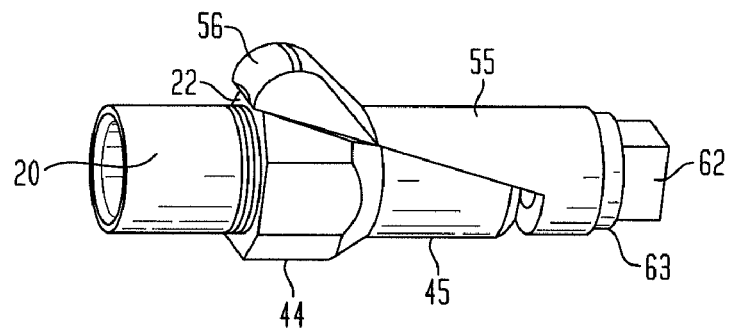
FIG. 3 is a perspective view of the joint according to FIG. 2 in an assembled state.

Fixation screw 60 can be turned into the ball-nut 30. This operation tightens the screw 60 and reduces the relative distance of sleeve 20, blocking element 40 as well as ring insert 50 one to another. This movement presses ball 22 into socket 41 and the ball joint/rotation movement of the joint is locked. In other words: tightening screw 60 blocks the determined orientation of the axis of ring insert 50 in relation to the axis of sleeve 20. The orientation is shown in FIG. 2 to 4 to be identical, being the same axis. FIG. 1 shows different orientation in the context of the use of a strut 10 comprising two of these ball joints 12.

The clamping action is generated due to friction and an additional shape fitting because the ball 22 has hardened ribs 24 that dig into the softer opposite shape of the socket 41. Ribs 24 describe concentrical rings around the axis of sleeve 20, wherein the envelope of the ribs in longitudinal direction of the sleeve 20 comprises a portion of a sphere with intervening grooves 25. Different materials are used for elements 20 and 40; especially sleeve 20 is harder than blocking element 40. This ensures that the hard ribs are digging into the softer socket 41 of the blocking element 40, providing for a positive fit. It would be possible to separately harden the ball portion 25.

Inside the sleeve 20 is arranged ball nut 30. The central bore 23 through sleeve 20 has two different portions. The first one is simply big enough to allow introduction of ball nut 30. The second portion is a spherical portion forming a hollow ball portion 26 which is concentrical to the sphere of the ribs 24.

One portion of the bore inside blocking element 40 is complementary to the polygon cylinder 32 of ball nut 30 to allow accommodating ball nut 30 in a rotation-free manner inside of blocking element 40 in the area of the cylindrical portion 45, i.e. behind the socket 41.

Thus it is possible to turn screw 60 and block the ball portion 22 of sleeve 20 inside the complementary socket 41 of the blocking element 40. Since all three clamping elements, the ball nut 30, the spherical portion 26 of sleeve 20 as well as the spherical socket 41 of blocking element 40 have the same center point, the device can be oriented in every angle, especially up to nearly 20° inclined against the axis of screw 60, i.e. the main axis of the ball joint 12 being. In a use position, parallel to a hole in the fixator. Usually a range between 0° and 15° is contemplated and can be achieved by form of the spherical portion 22.

FIG. 3 shows a perspective view of the joint 12 according to FIG. 2 in an assembled state. Similar features of the joint 12 receive the same reference numerals in all drawings. FIG. 4 shows a cross section of the joint 12 according to FIG. 2 in its longitudinal direction.

The second object of the ball joint 12 is to connect the joint, being connected to the rod 11 of a strut 10, to a hole of a plurality of holes inside a ring of an external fixator. This contact is realized with the help of shaft or cylindrical portion 55 of the blocking ring insert element 50. Although it is possible to provide a polygonal, elliptical or another rotation resistant exterior form of the blocking ring insert element 50, which would have complementary polygonal, elliptical or other rotation resistant interior form of the hole of an external fixator, it is preferred to use a cylindrical blocking ring insert element 50 and a cylindrical hole in the ring of the external fixator.

The element allowing for blocking the shaft 55 of the blocking element 50 inside the hole of the external fixator is the wedge surface comprising the two inclined surfaces 42 and 52 of the blocking element 40 and ring insert 50, respectively. Blocking element 40 and ring insert 50 can be arranged in a way that their exterior cylindrical surfaces 55 and 45 respectively fit inside the hole of the ring fixator. By tightening the screw 60 the blocking element 40 and the ring insert 50 are moving together in axial direction. Because of the flat wedge portions 42 and 52 the two elements 40 and 50 increase their radial distance, in other words the two diametrically opposed cylindrical portions 55 and 45 do not have the same central axis any more but are in a equal distance in the longitudinal direction of the blocking element 40 and the ring insert 50. Therefore they compress inside the ring hole and the fix connection of the ball joint 12 or this end of strut 10 with the ring hole is realized.

Because the screw 50 fixes simultaneously the ball joint and the cylinder to the ring hole, there is only one tightening step necessary.

The wedge has a predetermined angle. This angle is usually chosen between 8° and 20° preferably between 10° and 15°, so that it is self locking within the ring hole after a first tightening operation. When the ball joint 12 is fixed within the ring hole and the screw 50 is released or untightened, then the joint stays fixed within the ring hole although the rotation of the ball joint itself, via ball nut 30 is released. It is then necessary to turn the sleeve 20 with help of a wrench engaging the tetragon or octagon loosening surface 44, the self locking becomes loosened and the ball joint 12 can be removed from the ring hole.

Additionally, on ring insert 50 there is provided a nose portion 56 to push ring insert 50 down the wedge surface 42/52 if possible without engagement of an instrument. Furthermore said nose portion 56 provide a shoulder, guaranteeing that the cylindrical portions 45 and 55 being smaller, there is no risk that the ball joint 12 is falling through a hole of a fixator rod 11.

Figure 5:
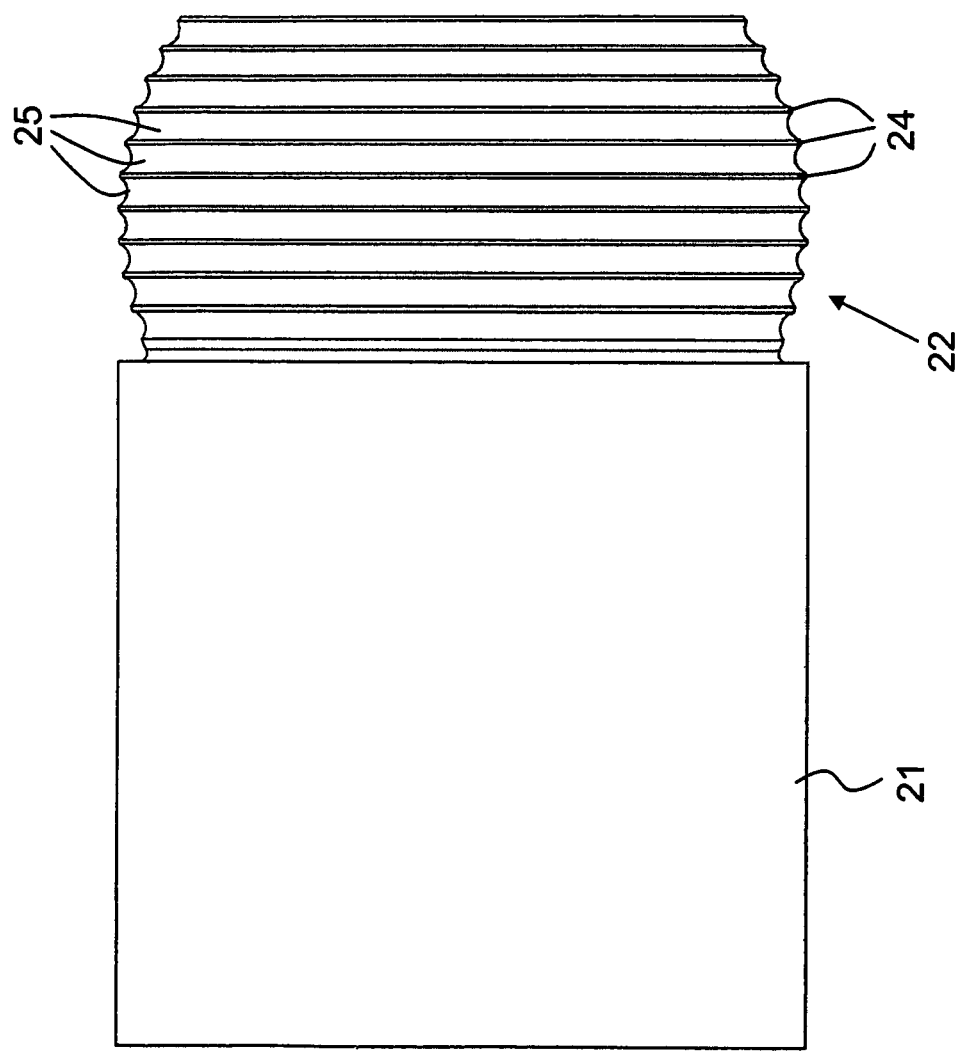
FIG. 5 is an enlarged side view of the sleeve of the joint according to FIG. 2.

FIG. 5 shows an enlarged side view of the sleeve 20 of the joint 15 according to FIG. 2, showing that the embodiment uses ten ribs 24 with nine intervening grooves 25. The largest portion of spherical portion 22 has a smaller diameter than the cylindrical portion 21 and the inner diameter of the spherical portion 22, i.e. the inner sphere, is unruffled and is smaller than the inner diameter of the sleeve 20 to allow introduction of ball nut 30 with its spherical portion 33 through bore 23.

Figure 6:
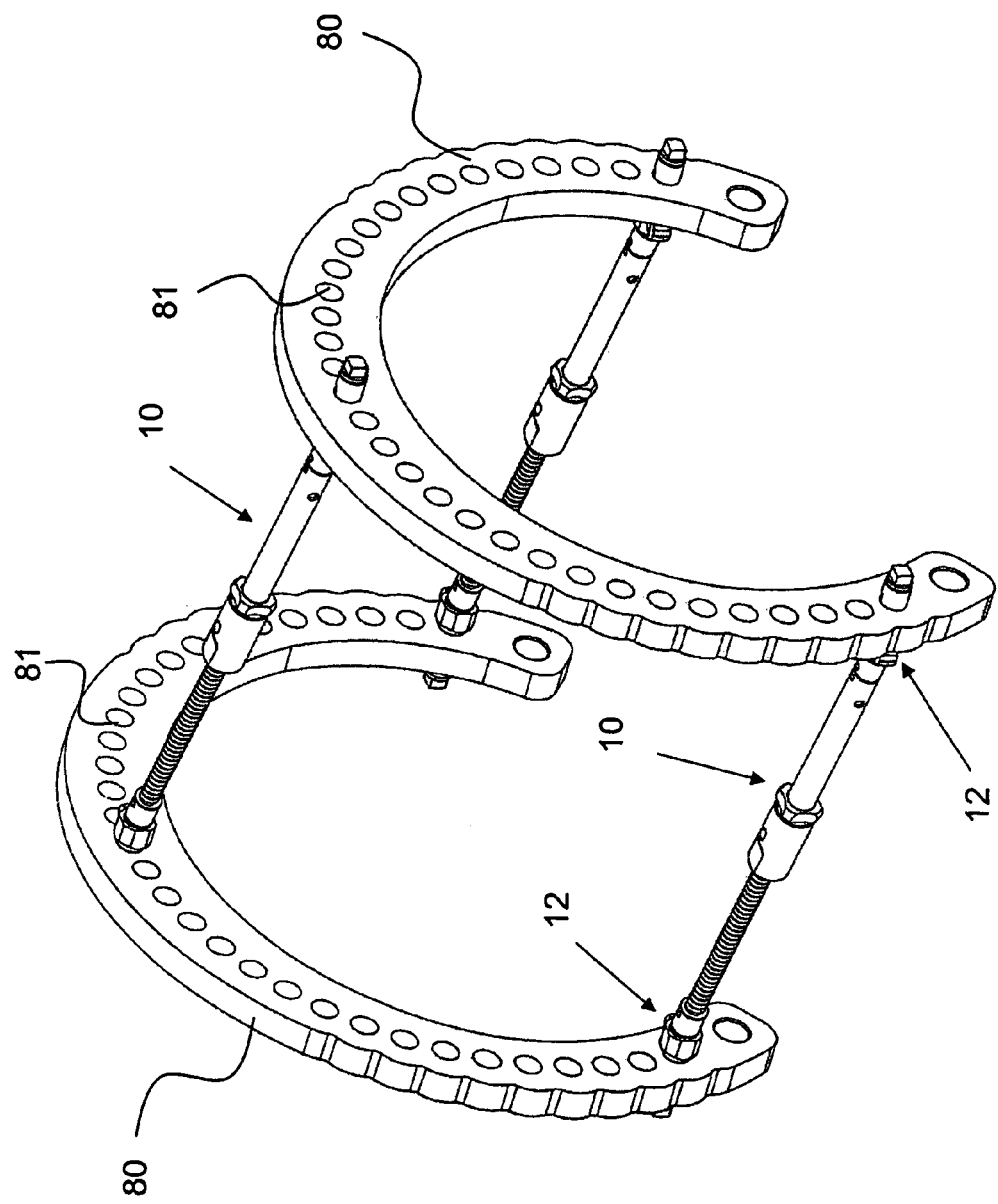
FIG. 6 is a perspective view of three struts according to FIG. 1 attached to two external fixator rings.

Finally FIG. 6 shows a perspective view of three struts 10 according to FIG. 1 attached to two external fixator rings 80. These rings 80 shown in FIG. 6 comprise a partial ring beam covering about 270 degree. Each ring 80 comprises a plurality of holes 81 having an internal diameter allowing to accommodate the cylindrical portion 55 of ring insert 50 in conjunction with the opposite cylindrical portion of blocking element 40. Actuation of fixation screw 60 expands the diameter of the unit provided by blocking element 40 and ring insert 50 and thus fixes the neck part 50/60 of the ball joint 12 within one of the holes 81 of a ring 80. It is clear from FIG. 6 that the two rings 80 can be moved one against the other, since all three struts 10 use two ball joints 12 at each of their free ends.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A strut for coupling two ring elements of an external fixator, comprising
   a rod,
   a sleeve coupled to the rod having inner and outer spherical portions;
   a ring insert having a wedge surface for insertion into a hole in a ring element;
   a blocking element having a wedge surface being complementary with the wedge surface of the ring insert and a spherical socket, wherein the outer spherical portion of the sleeve engages the complementary spherical socket of the blocking element,
   a ball nut having a spherical surface for engaging the inner spherical portion of the sleeve;
   a connection element having an end portion for engaging the ball nut;
   wherein the ring insert and the blocking element have a combined circumferential surface being adapted to be introduced into the hole of the external fixator ring element,
   wherein the complementary wedge surfaces allowing a relative axial displacement of ring insert and blocking element one against the other causes a radial expansion to enlarge the diameter of the combined circumferential surface for locking the ring element and blocking element inside the ring hole,
   wherein the connection element extends through the sleeve, the blocking element and ring insert into the ball nut and wherein the connection element and ball nut are arranged to activate the radial expansion upon an axial displacement therebetween.

2. The strut according to claim 1, wherein said combined circumferential surface is adapted to be introduced into a hole of a ring of an external fixator.

3. The strut according to claim 1, wherein the connection element is a screw providing an abutment surface for the ring insert as well as an outer thread engaging an inner thread of the ball nut.

4. The strut according to claim 1, wherein the blocking element comprises an inside bore which is not rotation-symmetrically constructed, wherein the ball nut, having a complementary outer surface can be introduced to allow only axial movements of the unit ball nut and connection element.

5. The strut according to claim 1, wherein wedge surfaces allowing a relative radial displacement of ring insert and blocking element are plane inclined surfaces.

6. The strut according to claim 1, wherein the inclination angle of the wedge surfaces is identical for the ring insert and, the blocking element is a self locking angle and lies between 8° and 20°.

7. The strut according to claim 1, wherein a spring is provided between the connection element and the ring insert for biasing the wedge surfaces.

8. The strut according to claim 1, wherein the ring insert further comprises a nose portion to allow manual compensation of the bias force of the spring.

9. Strut according to claim 1, wherein the blocking element further comprises a tool engagement loosening surface for rotating the blocking element against the ring insert.

10. A strut for an external fixator comprising at least one ball joint and a connecting rod being in engagement with said ball joint, wherein said strut comprises:
    a sleeve having a hollow ball portion with concentrical inner and outer spherical portions;
    a ring insert having a wedge surface;
    a blocking element having a wedge surface being complementary with the wedge surface of the ring insert and a spherical socket, wherein the outer spherical portion of the sleeve engages the complementary spherical socket of the blocking element,
    a ball nut which is in an engagement with said inner spherical portion;
    a connection element;
    wherein the sleeve is engagement with said rod,
    wherein said ring insert and said blocking element have a combined circumferential surface being adapted to be introduced into a hole of an external fixator element,
    wherein the complementary wedge surfaces allow a relative radial displacement of the ring insert and the blocking element against one another to enlarge the diameter of the combined circumferential surface for blocking the strut inside said hole,
    wherein said ball nut is in an axial displaceable relationship with said connection element extending in and through, the sleeve, the blocking element and the ring insert, wherein said connection element is arranged to activate said radial displacement and axial displacement.

11. The strut according to claim 10, comprising one ball joint at each end of a central connecting rod, being in engagement with said rod.

* * * * *

UNITED STATES PATENT AND TRADEMARK OFFICE
CERTIFICATE OF CORRECTION

PATENT NO. : 8,062,293 B2
APPLICATION NO. : 12/288332
DATED : November 22, 2011
INVENTOR(S) : Christian Steiner et al.

It is certified that error appears in the above-identified patent and that said Letters Patent is hereby corrected as shown below:

In the Specifications

Column 2, line 16, "joint and with the joint the rod and" should read --joint with the rod and--.

Column 4, line 33, "fix connection of the ball joint 12 or this" should read --fixed connection of the ball joint 12 and this--.

Signed and Sealed this
Twenty-third Day of April, 2013

Teresa Stanek Rea
*Acting Director of the United States Patent and Trademark Office*